US008926626B2

(12) United States Patent
Mannava et al.

(10) Patent No.: US 8,926,626 B2
(45) Date of Patent: Jan. 6, 2015

(54) TISSUE TENSIONING DEVICES AND RELATED METHODS (75) Inventors: Sandeep Mannava, Winston-Salem, NC (US); Martin L Tanaka, Cullowhee, NC (US); Christopher J. Tuohy, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 673 days.

(21) Appl. No.: 12/942,311

(22) Filed: Nov. 9, 2010

(65) Prior Publication Data

US 2011/0112570 A1 May 12, 2011

Related U.S. Application Data (60) Provisional application No. 61/259,839, filed on Nov. 10, 2009, provisional application No. 61/285,395, filed on Dec. 10, 2009.

(51) Int. Cl.
*A61B 17/58* (2006.01)
*A61B 17/60* (2006.01)
*A61F 2/00* (2006.01)
*A61B 17/28* (2006.01)
*A61B 19/00* (2006.01)

(52) U.S. Cl.
CPC ....... *A61B 17/2812* (2013.01); *A61B 2019/464* (2013.01)
USPC .......................................... 606/102; 606/205

(58) Field of Classification Search
CPC ........... A61B 17/2812; A61B 17/2816; A61B 17/7022; A61B 2019/464; A61B 2019/2246; A61B 19/46

USPC .......... 606/124, 102; 600/202, 306, 200, 587; 33/747, 750, 751, 752, 787, 797, 798, 33/799, 800, 701

See application file for complete search history.

(56) References Cited

U.S. PATENT DOCUMENTS

| 2,715,403 | A | * | 8/1955 | Jordan | 606/201 |
| 4,834,752 | A | | 5/1989 | Van Kampen | |
| 4,893,619 | A | * | 1/1990 | Dale et al. | 606/87 |
| 4,950,271 | A | * | 8/1990 | Lewis et al. | 606/102 |
| 4,964,862 | A | | 10/1990 | Arms | |
| 4,969,471 | A | * | 11/1990 | Daniel et al. | 600/587 |
| 5,289,826 | A | | 3/1994 | Kovacevic | |
| 5,713,897 | A | * | 2/1998 | Goble et al. | 606/53 |
| 5,997,545 | A | * | 12/1999 | Doherty et al. | 606/102 |
| 6,001,106 | A | | 12/1999 | Ryan et al. | |
| 6,013,083 | A | | 1/2000 | Bennett | |
| 2001/0049483 | A1 | | 12/2001 | Reay-Young | |
| 2004/0153083 | A1 | * | 8/2004 | Nemec et al. | 606/86 |

OTHER PUBLICATIONS

Arthrex, Double Row Rotator Cuff Repair using the Bio-Corkscrew® FT, © Copyright Arthrex Inc., 2007, 6 pages.
International Search Report and Written Opinion for corresponding PCT Application No. PCT/US2010/055904, Date of mailing May 25, 2011.

* cited by examiner

*Primary Examiner* — David Bates
*Assistant Examiner* — Samuel Hanna
(74) *Attorney, Agent, or Firm* — Myers Bigel Sibley & Sajovec, P.A.

(57) ABSTRACT

Surgical devices configured to apply and hold a defined preset or pre-load tension to target tissue, such as, for example, a blood vessel, tendon or ligament during a surgical procedure.

16 Claims, 9 Drawing Sheets

TISSUE TENSIONING DEVICES AND RELATED METHODS

RELATED APPLICATIONS

This application claims the benefit of and priority to U.S. Provisional Application Ser. No. 61/259,839 filed Nov. 10, 2009 and U.S. Provisional Application Ser. No. 61/285,395 filed Dec. 10, 2009, the contents of which are hereby incorporated by reference as if recited in full herein.

FIELD OF THE INVENTION

This invention relates to surgical devices.

BACKGROUND OF THE INVENTION

It is estimated that over 30 million musculoskeletal injuries occur every year in the United States. It is believed that over 50% of these injuries involve soft tissue tears (e.g., tendons). Unfortunately, some of these tissues will re-tear after surgical repair. For example, rotator cuff surgery has a very high rate of re-tearing (estimated at between about 20-70%). Conventionally, surgeons repair the tendons based on experience and "feel". Various tissue grasper devices used to repair tendons are known but there remains a need for devices that can effectively measure and hold proper tension in order to promote healing of skeletal muscle and reduce the incidence of re-injury.

SUMMARY OF EMBODIMENTS OF THE INVENTION

Embodiments of the invention are directed to devices and methods for measuring (pre-load) tension applied to target tissue during surgery.

Some embodiments are directed to surgical devices that include: (a) a tissue grasper; (b) a tension measurement device in communication with the grasper whereby tension applied to tissue by the tissue grasper is measured; and (c) a limb mounting member configured to support the tissue grasper and releasably hold the surgical device on a limb of a patient.

Other embodiments are directed to surgical devices for rotator cuff repair surgeries. The devices include: (a) a soft-tissue grasper configured to pull rotator cuff tendon associated with the rotator cuff repair; (b) a tension measurement device in communication with the grasper whereby tension applied to the rotator cuff tendon by the grasper is measured; and (c) a circuit in communication with the tension measurement device configured to define a target pre-load tension.

Additional embodiments are directed to methods of repairing a rotator cuff injury. The methods include: (a) providing a device with a tissue grasper and a tension measurement device; (b) pulling a detached torn rotator cuff down from a retracted intrabody position using the tissue grasper; (c) measuring tension applied to the rotator cuff during the pulling step using the tension measurement device; then (d) maintaining a desired defined pre-load tension on the pulled rotator cuff using the device while affixing the rotator cuff to local bone.

Still other embodiments are directed to surgical devices that include tissue graspers, a tension measurement device in communication with the tissue graspers and a tissue elongation guide in communication with the tissue graspers to measure elongation of tissue held by the tissue graspers.

The device may include a circuit in communication with the tension measurement device configured to generate an audible and/or visual output when a target pre-load is met or exceeded.

The tissue graspers can be in communication with a releasably lockable gimble that can allow a user to pivot and lock the tissue graspers into a desired orientation.

The device may include a circuit in communication with the tissue elongation guide and the tension measurement device, the circuit configured to: (a) monitor the measured tension; (b) generate an output to a user when a target pre-load tension is approached, met and/or exceeded; and (c) measure tissue stiffness using data from the measured tension and data from the tissue elongation guide.

Embodiments of the invention are directed to methods of repairing a tissue injury. The methods include: (a) providing a device with a tissue grasper and a tension measurement device; (b) pulling tissue from a retracted intrabody position using the tissue grasper; (c) measuring tension applied to the tissue during the pulling step using the tension measurement device; then (d) maintaining a desired defined pre-load tension on the pulled tissue using the device while affixing the tissue to local structure.

The methods may further include mounting the device to a patient prior to the pulling and measuring steps; and slidably extending, retracting and pivoting the tissue graspers while the device is mounted to the patient. The measuring step can be carried out at least twice before the maintaining step, so that at least two different tension measurements are taken with the limb in at least two different positions.

The methods may include measuring tissue elongation of the pulled tissue using the device.

The foregoing and other objects and aspects of the present invention are explained in detail in the specification set forth below.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIGS. 10A-10C are schematic illustrations of examples of User Interfaces for the device shown in FIG. 9. FIG. 10C illustrates a graph of different angles of orientation (where used) with two lines that electronically compare tension applied to target pre-load tension according to embodiments of the present invention.

DESCRIPTION OF EMBODIMENTS OF THE INVENTION

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein.

Embodiments of the present invention contemplate that repairing tissue (e.g., a torn or damaged tendon of a muscle-tendon unit) using a defined pre-set (pre-load) tension in a reliable and quantifiable manner will improve surgical outcomes and/or reduce re-tearing of soft tissue. In physiology, pre-load tension is important to muscle function. Too little tension or too much tension can cause inefficient and/or inadequate muscle force generation. It is believed that an injured tendon-muscle unit will have an optimal preload repair tension that can improve healing potential post-surgery. It is also believed that the optimum tension may better line up the actin-myosin cross-bridging of the myofibrils. Embodiments of the present invention provide devices that allow a surgeon to quantify the repair tension and possibly manipulate the muscle-tendon unit during repair surgery in a way that optimizes the repair tension. Embodiments of the present invention can also allow a scientist to evaluate the effect of repair tension on muscle-tendon healing/remodeling after tendon injury.

The terms "pre-load" and "pre-set" are used interchangeably and refer to a defined or specified tensile force or load (or range thereof) is applied that target tissue should exhibit when attached to local structure to promote healing and/or structural integrity. The target tissue can be soft tissue or hard tissue (e.g., bone). For example, it is contemplated that a rotator cuff undergoing surgical repair should be attached to the humerus head with a pre-load of between about 0.25 $lb_f$ (about 1 N) to about 2 $lb_f$ (about 9 N) when the repaired cuff is attached to the humerus head and the arm is adjacent and substantially parallel to the patient's torso. However, embodiments of the present invention are not limited by the actual pre-load values but contemplate that a specified pre-load is applied. Actual pre-load values can vary depending on specific parameters of each patient.

The target pre-load may differ depending on gender, age and the like of a patient as well as the soft tissue and/or bone undergoing repair. Thus, an anterior cruciate ligament (ACL) may have a different optimal pre-load than a rotator cuff, even in the same patient.

Embodiments of the invention are useful for veterinarian and human uses as well as for animal studies. That is, methods and devices provided by embodiments of the invention can be configured for any species of interest, e.g., mammalian including human, simian, mouse, rat, lagomorph, bovine, ovine, caprine, porcine, equine, feline, canine, and the like.

Although described primarily for use with torn or otherwise damaged tendons, it is contemplated that the devices and methods will be useful for generating, measuring and maintaining a desired tension force in tendons, ligaments, nerves, tubular vessels (e.g., a ureter or blood vessel), the dermis, bone, flap (tissue) surgery (full thickness, partial thickness and the like) and hard tissue. The devices and methods can be configured to apply, measure and/or maintain tension on a combination of the anatomical structures during a surgical procedure or an animal study.

Embodiments of the invention can also or alternatively electronically measure stiffness. Stiffness may be directly or indirectly determined by the tendon tension and tendon extension relationship.

Embodiments of the devices can also or alternatively be used to measure a change in length of tissue along with or in response to the applied tensioning (e.g., tendon extension). The measurement can be electronically performed using, for example, a proximity sensor that can communicate with grasped tissue held by the graspers 15 (FIGS. 1-5) to assess a change in length in relationship to a stationary portion of the device 10. The change in length can be relayed to a display (on-board and/or remote such as those discussed below).

The devices can be configured for arthroscopic, robotic and/or conventional open surgery.

The term "tissue" refers to soft tissue (e.g., nerves, blood vessels, ligaments, tendons, colon, intestine and the like) and hard tissue (e.g., bone).

Referring now to the figures, FIGS. 1-5 illustrate one embodiment of a surgical device 10. As shown, the device 10 includes a tissue grasper 15 attached to an elongate member 17 that communicates with a tension measurement device 20. The tissue grasper 15 can be configured as a clamp-like member with prongs or ends that form substantially an "L" shape as shown. However, other configurations of the tissue grasper 15 can also be used as appropriate. One or both inside faces of the grasper (that contact and hold tissue) can include an anti-slip surface. This surface can be formed as a rough surface finish, include an anti-slide coating or material, and/or have an uneven surface configuration (e.g., peak and valley type surface) to inhibit slippage. The elongate member 17 can be a substantially rigid shaft as shown or may be a cable, such as a Bowden cable. Combinations of shafts and cables may also be used. Where cables are used as the external component, the end of the cable can be attached to the bone using a screw or other fixation device so that the cable does not move with respect to the tendon so that tension can be measured.

Figure 7:
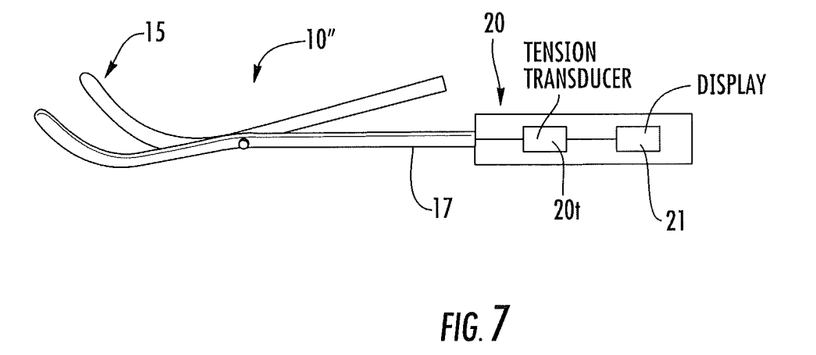
FIG. 7 is a schematic illustration of another embodiment of a device which may be configured as a hand supported embodiment or as a limb-mounted embodiment according to embodiments of the present invention.

The tension measurement device 20 can be mechanical and/or electromechanical, including, for example, one or more of the following: a tension transducer, a tension meter (including a digital tension meter), and a load cell. The tension measurement device 20 can reside in a housing 19 that can include graduated indicia 20I of tensile load applied by the tissue grasper 15 to local structure. Alternatively, or additionally, the device 10 can include a display 21 that provides tensile load readout to a user (FIG. 7).

As shown, a portion of the shaft 17 is held in a housing 19 with a resilient member 22, shown as a coil spring 22s. The resilient member 22 is able to elastically compress, typically linearly, against an inner wall or surface of an inner housing 24. The resilient member 22 can be a plug or block of elastomeric material, and/or one of a plurality of spring washers, dome washers, leaf springs, coil springs and the like. As shown in FIGS. 1-5, the resilient member 22 is a coil spring 22s. The elongate member 17 extends through an axially extending channel formed by the coil 22s and is able to slidably extend in and out of the end of the housing 19 facing the graspers 15.

Figure 1:
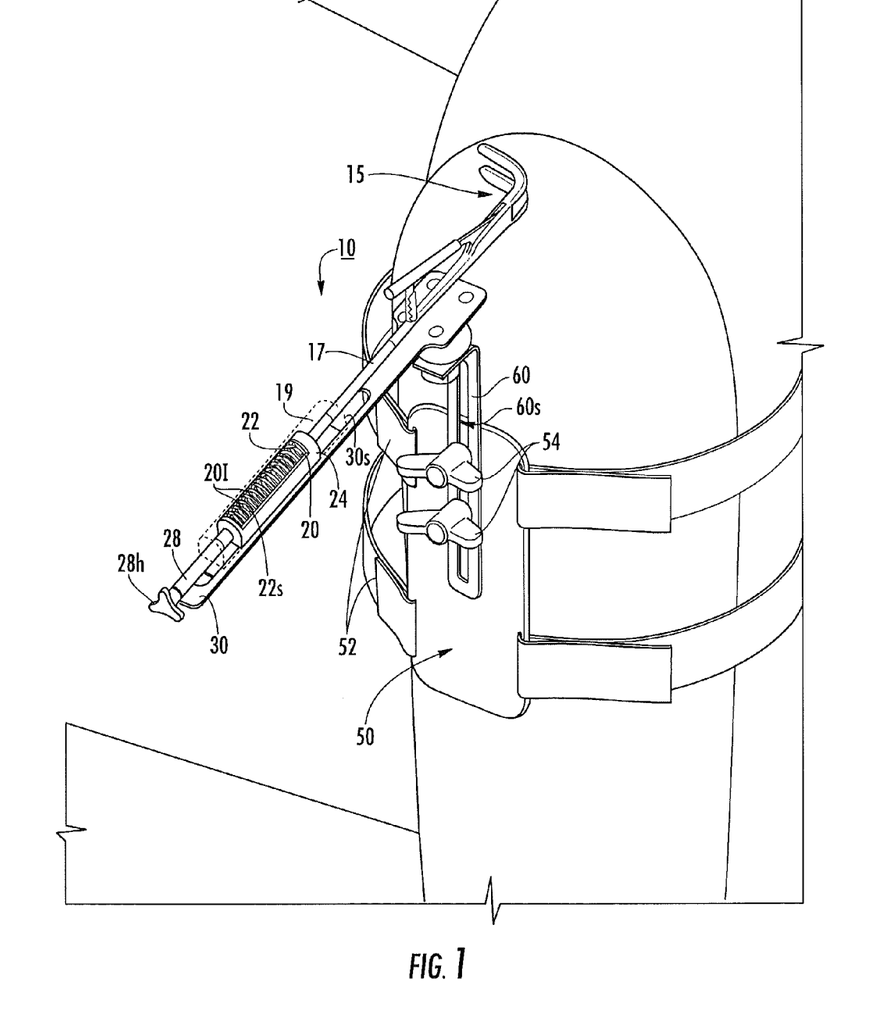
FIG. 1 is a top perspective view of an exemplary device (shown mounted on a patient) according to some embodiments of the present invention.
Figures 2A, 2C:
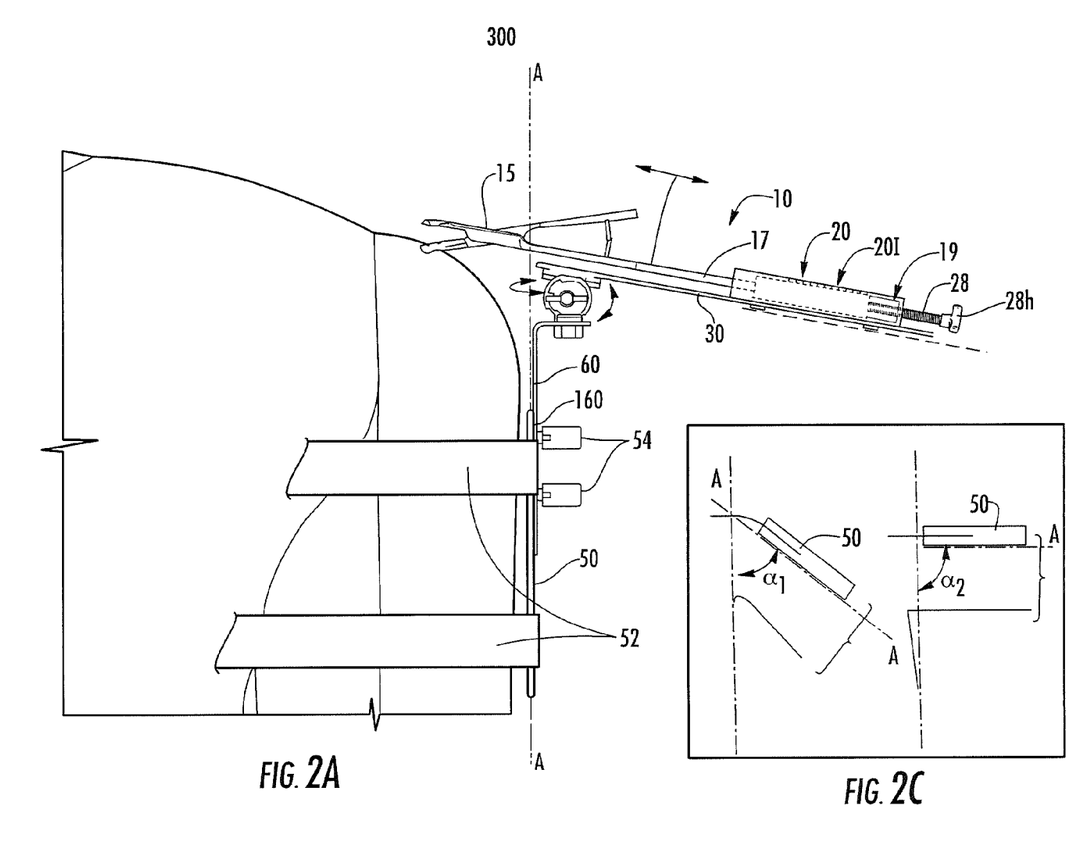
FIG. 2A is a side view of the device shown in FIG. 1 also illustrating an optional angle measurement device according to some embodiments of the present invention.
FIG. 2C is a schematic illustration of exemplary angle positions of a limb which can be electronically measured according to some embodiments of the present invention.
Figures 2B, 3:
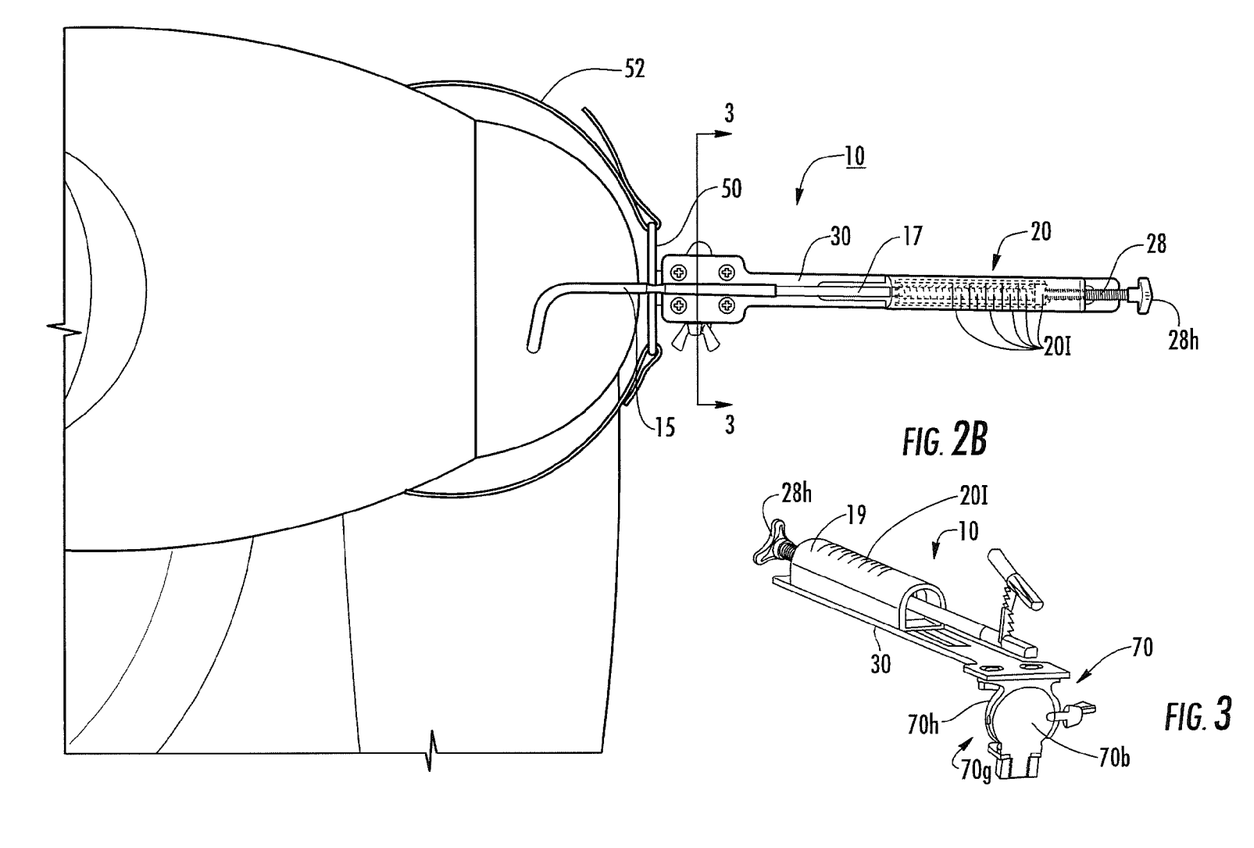
FIG. 2B is a top view of the device shown in FIG. 1.
FIG. 3 is a partial section view of a portion of the device shown in FIG. 1 taken along line 3-3 in FIG. 2B.

FIG. 3 illustrates that the elongate member (e.g., shaft) 17 can reside above a platform 30 with a slot 30s. The housing 19 can slide in the slot 30s. The platform 30 includes opposing ends 31, 32. The slot 30s extends at least a major length of the platform and ends proximate the second end 31 (the end away from the graspers 15). The graspers 15 can extend beyond the bounds of the other end of the platform 32. As one alternative to this configuration, the platform 30 can be configured to have an outwardly extending projection that engages a slot extending in a lengthwise direction in the housing 19 to allow the graspers 15 to slidably extend and retract relative to the platform 30 (not shown). Other sliding configurations may also be used.

Figure 4A:
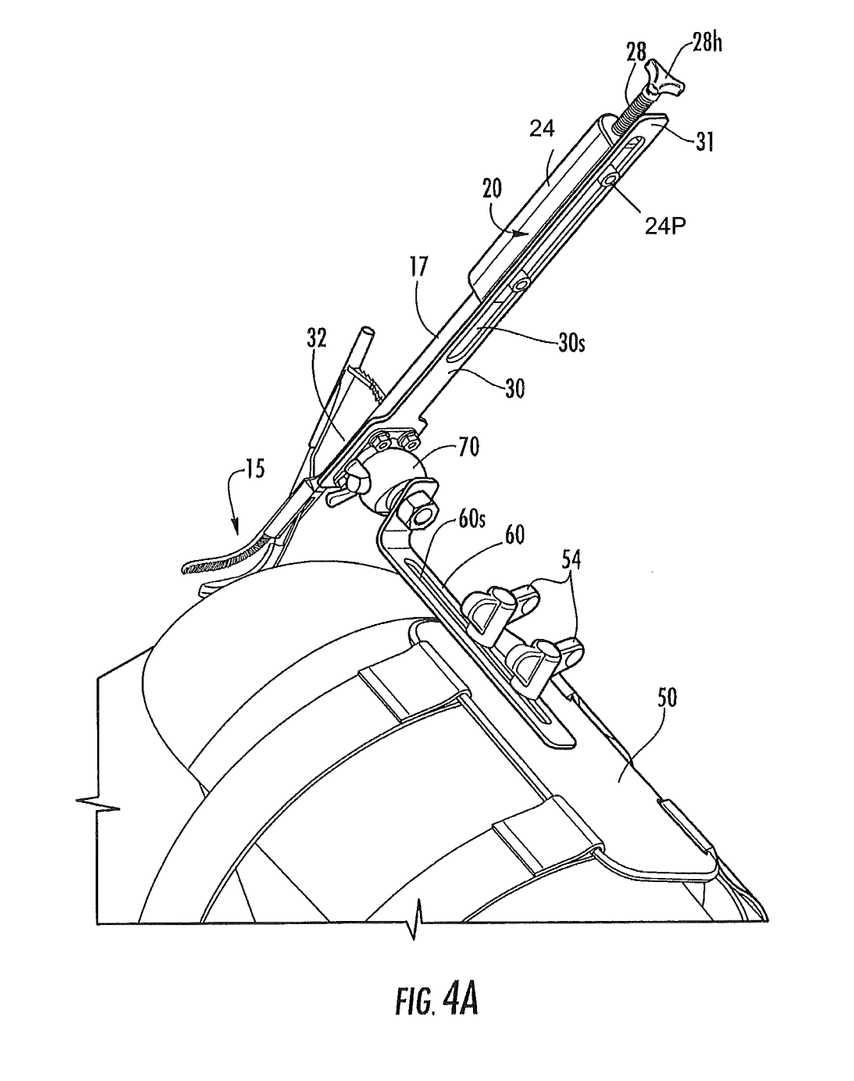
FIG. 4A is a bottom perspective view of the device shown in FIG. 1.
Figure 4B:
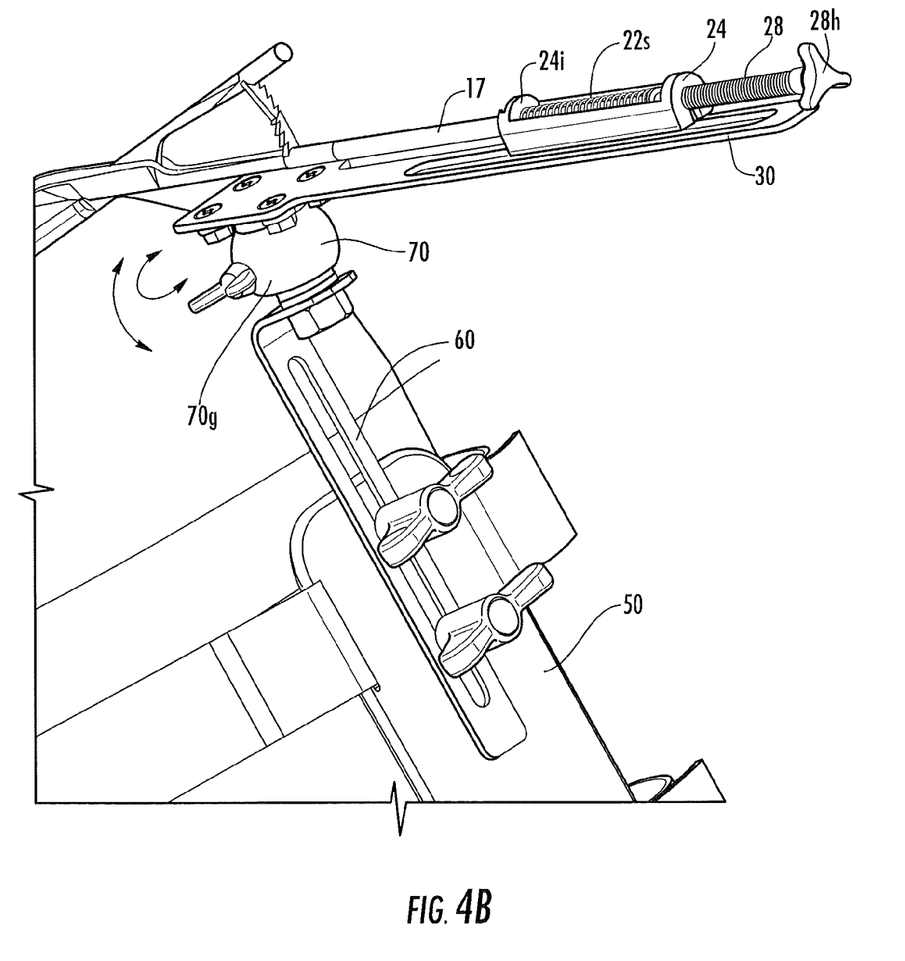
FIG. 4B is a side perspective view of the device shown in FIG. 1, illustrated without an outer housing.
Figure 5:
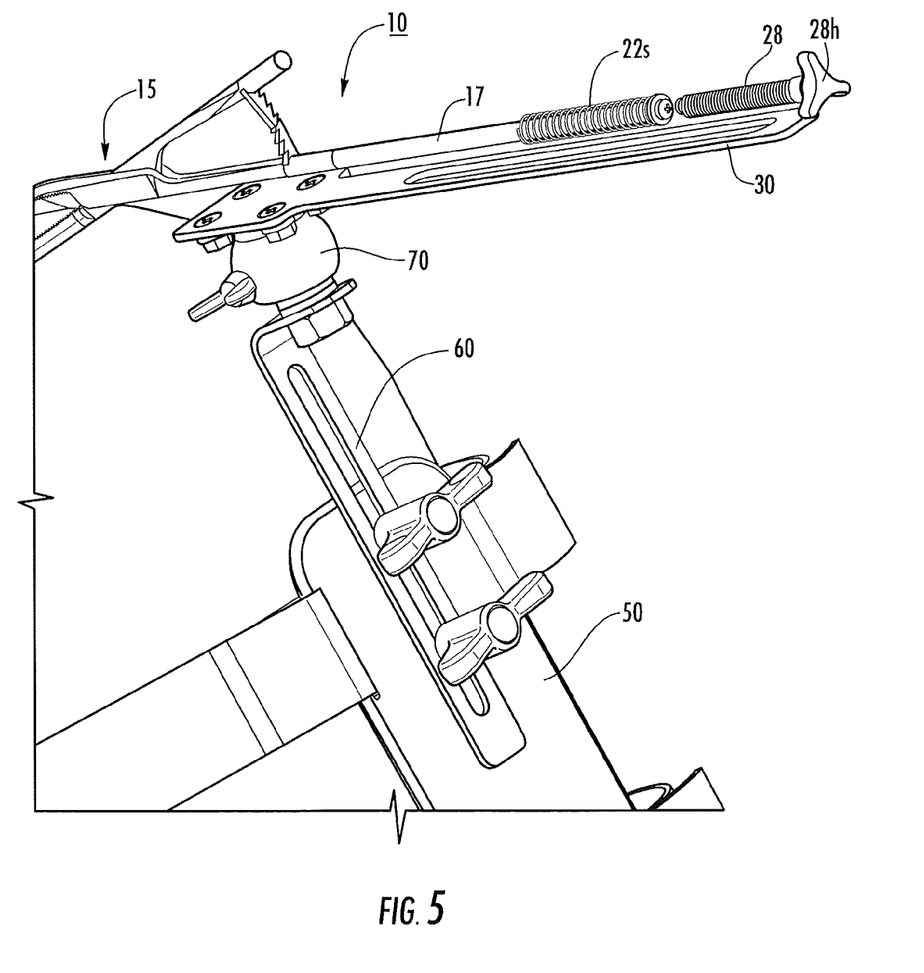
FIG. 5 is a side perspective view of the device shown in FIG. 1, shown without the outer housing (guide) and the inner housing.

As shown in FIGS. 3-5, the device 10 can also include a threaded shaft 28 that communicates with a user accessible handle 28h such as a thumb wheel or other user handle that allows a user to turn the threaded shaft 28. FIGS. 4A and 4B illustrate the inner housing 24 without the guide 19 (the guide may also be described as an outer housing). The inner housing 24 can slide using downwardly extending projections 24p in the slot 30s within the guide 19. In operation, the housing 24 is pulled back (toward the handle 28h) by turning the threaded member 28 causing the housing 24 to slide within guide 19 and causing the threaded member 28 to contact and increase compression on resilient member 20, shown as the coil spring 22s, pushing the resilient member 20 (such as the coil spring 22s) against the inner wall 24i (FIG. 4) of the housing 24 resulting in increased tension on the grasped tendon or other tissue. The tension is identified on a display 21 (FIG. 7) and/or by the graduated indicia 20I on the guide 19.

In some embodiments, the resilient member 20 comprises a coil spring 22s with a "K" stiffness value sufficient to generate a tension of up to about 15 $lb_f$ (about 67 N) in a limited travel/displacement of between about 1-10 inches.

During use, a physician or other clinician can slidably extend the tissue grasper 15 to contact and grasp target tissue such as a retracted rotator cuff in the body. When the grasper is closed, the handle 28h can be turned to pull the closed graspers 15 outward while applying a tension at a defined load using the tension measurement device 20. This type of operation may be referred to as a two-stage process. The first stage is extending the graspers 15 to contact the desired tissue. The second step is to measure tension as the tissue is pulled into position during surgery and held at the position with the pre-load tension while the tissue is secured in the position with this pre-load. A clinician can then suture, screw, staple or otherwise secure the target tissue to local structure so that, when secured, the attached target tissue substantially has the desired pre-load tensile force.

FIGS. 1-5 illustrate that the device 10 can be limb-mounted using a limb mount member 50 that can be belted or strapped to a patient using strap/belts 52. The device 10 may also or alternatively be configured to cooperate with a pole or bed (e.g., a pole, table, cart or bed mounted version). That is, the device can include a mount member that attaches to a pole, table, cart or bed instead of the patient limb or in combination with the limb mount (not shown).

Where used, the limb mount member 50 may alternatively or additionally be adhesively attached to a patient using straps 52 that have an adhesive surface for releasably attaching to the skin of a patient. Additionally or alternatively the body of the support 50 may have an adhesive on a patient-contacting surface. It is also envisioned that the support 50 may also be modified to be torso mounted. The limb mount member 50 can be concave or contoured to fit the target limb. The limb mount member 50 can be provided in various sizes to accommodate different size patients (e.g., S, M, L, XL).

The straps 52 can comprise cloth, fabric, leather or other suitable, typically elastic, material and/or combinations thereof. The straps 52 can be configured to inhibit slippage. The straps 52 can be substantially planar or may be tubular (e.g., a rope-like) configuration or other suitable configuration that has a length sufficient to encircle or extend about the torso and/or limb of a subject. The straps 52 may be provided in S, M, L and XL sizes to fit different anatomical sizes of people or may be provided in a universal size. The straps 52 can be attached to clasp or buckle that allows for almost any desired adjustable length.

The device 10 can mount to the limb using a joint 70 that allows lateral and longitudinal rotational (pivoting) movement about an axis so that the tensile force can be measured while a patient's limb is moved through a variety of different angles or orientations (from 0, 15, 30, 45, 60 and 90 degrees) without requiring that the tissue grasper 15 release the tissue. The tension force measurement device 20 may be zeroed at different orientations/degrees.

As shown in FIG. 2A, the device 10 can also optionally be configured to electronically measure an angle of inclination 300 of the arm or other limb associated with axis "A-A" which in FIG. 2A is substantially vertical ("0" degrees of inclination) with the arm at the side of the patient. The limb mount 50 can include an angle measurement device 160 (e.g., optical, electrical or electro-mechanical) that communicates with a read-out and/or display on-board or remote from the device 10. The measurement device 160 can be integral with the body of the limb mount 50 or attached to the extension member 60 or otherwise be provided to be able to measure the different angles of inclination during a procedure. The device 10 may have a User Interface that allows a user to affirmatively indicate when the device should measure tension at a certain angle of orientation (e.g., "measure now") which can cause the device to electronically measure (and record) both angle and tension. Thus, the tension "T" at different angles of inclination can be electronically measured and correlated. FIG. 2C schematically illustrates the device 10 with the arm at two additional angles of inclination "$\alpha 1, \alpha 2$". The different angles and the different measurements can be stored in a circuit/memory for ease of analysis of patient records or animal study data records.

As shown in FIG. 3, the joint 70 can comprise a gimble ball 70g. The term "gimble" refers to a pivoted support that allows the rotation of an object (here the graspers 15) in three-dimensions about a single axis. The hollow outer spherical member 70h can reside on a lower surface of the upper platform 30 and the matably engaging ball 70b can reside on an upper portion of the vertical support 60. In other embodiments, the ball and spherical members are reversed, e.g., the ball 60b is attached to the upper platform 30 and the spherical hollow member 70h is attached to the vertical member 60. The gimble 70g can be releasably locked into position. However, other joint configurations may be used such as, for example, a spring, pin, linkages, cams, gears or other pivoting or rotational configurations.

FIGS. 1-5 also illustrate that the device 10 can include a vertically extending adjustable member 60 that can attach the limb-mount member 50 to the platform 30 via the joint 70. The vertical adjustment member 60 can include a slot that attaches to locking members 54 on the limb-mount member 50.

Figure 6:
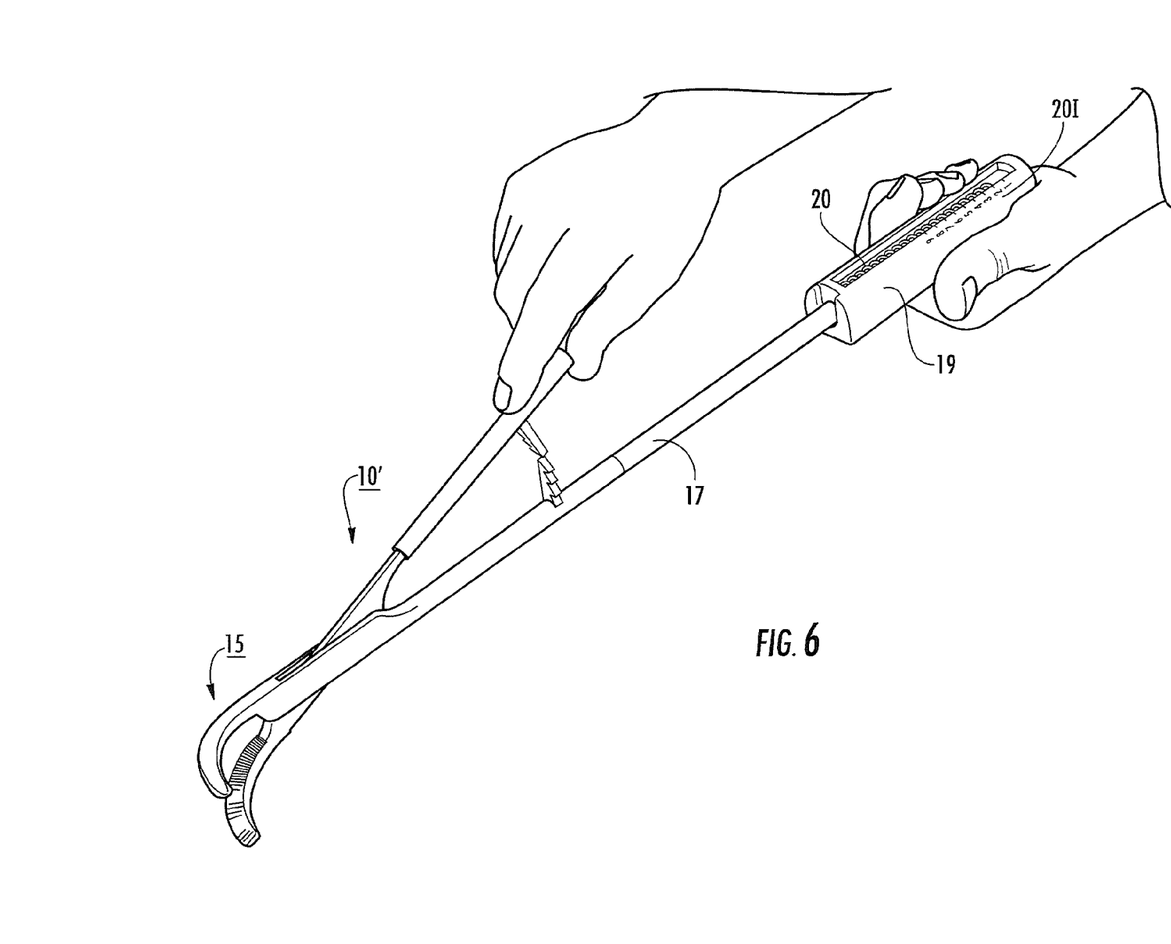
FIG. 6 is a top side perspective view of another embodiment illustrating the device may be hand supported.

FIG. 6 illustrates that the device 10' can be hand-supported during use and does not require the limb mount described above. During use, one physician (or a physician assistant, nurse or other clinician) can hold the device in position at the desired pre-load tension during the repair while another secures the target tissue to local structure(s). The device 10' may also be configured to cooperate with a pole, cart, table or bed (e.g., a pole or bed mounted version) as well (not shown).

FIG. 6 also illustrates that a user can measure applied tension "T" by monitoring the indica 20I (e.g., graduated scale) on the tension measurement device 20. No threaded member 28 or handle 28h is required. The body of the housing 19 can slide rearward compressing a resilient member 20 and the position of an indicator on the shaft or other elongate member 17 can align with indicia 20I to define the tensile load applied by the graspers 15. This configuration can also be used with a limb mount 50 as described above or with a pole or bed mount.

FIG. 7 illustrates a device 10'' which includes a tension measurement device 20, such as a transducer 20T, in communication with the graspers 15 via elongate member 17 (e.g., shaft or cable and the like). The device 10'' can include an on-board display in electrical communication with the transducer 20T which can visually show the measured tension. Again, the device 10'' may include a limb mount 50 as discussed above or can be used with a pole or bed mount.

Figure 8A:
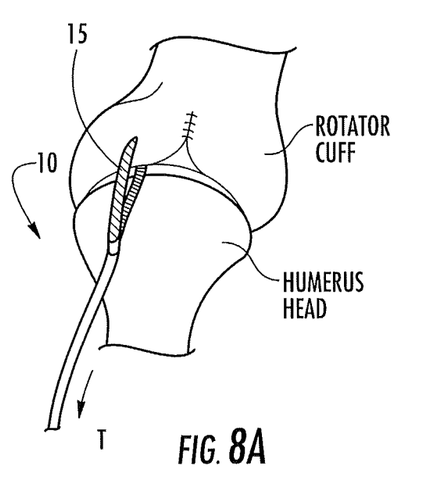
FIG. 8A illustrates a tissue grasper device applying a desired pre-load "T" onto a rotator cuff while the cuff is secured in position, typically to the humerus head.
Figure 8B:
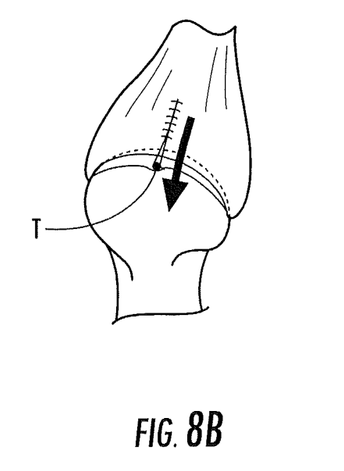
FIG. 8B illustrates that, after repair, the cuff substantially maintains the desired tensile pre-load "T" applied by the tissue grasper in FIG. 8A according to embodiments of the present invention.

FIGS. 8A and 8B illustrate an exemplary rotator cuff repair. As shown in FIG. 8A, the device 10, 10', 10'' is used to apply a pre-load tension "T" onto the tendon while a surgeon attaches the tendon to the humerus head. When the tendon has been attached to the humerus head as shown in FIG. 8B, the grasper 15 can release the tendon and the cuff has the desired pre-load "T".

Figure 9:
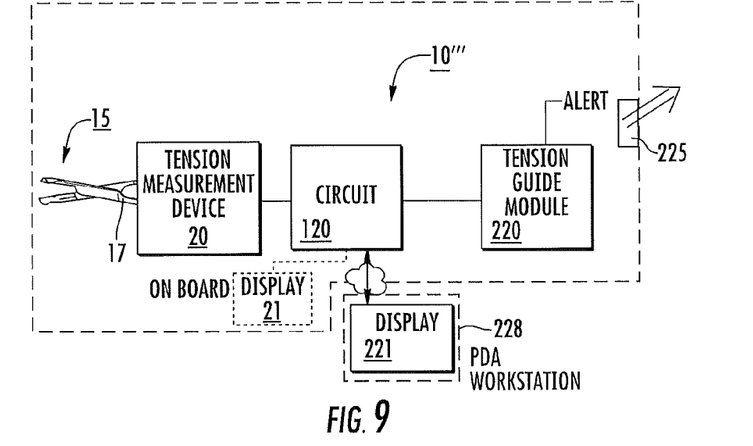
FIG. 9 is a schematic illustration of a device with a digital signal processor or ASIC that defines target (e.g., optimal) tensile loads for a given indication.

FIG. 9 illustrates another embodiment of the device 10''. As shown, the device 10''' includes the graspers 15 and an elongate member 17 that is in communication with a tension measurement device 20. The tension measurement device 20 can be any suitable type device such as those described above. The device 10''' can include a circuit 120 with an on-board digital signal microprocessor or ASIC (Application Specific Integrated Circuit) 120 that includes or communicates with a computer tension guide module 220 or is otherwise programmed to provide at least one defined pre-load tension, typically one or more defined pre-load tensions for one or a plurality of different target tissues (potentially correlated to gender and/or age). The device 10''' can optionally include an on-board display 21. The device 10''' can also be configured to wirelessly communicate with a (larger) remote device 228 with a display 221 such as a clinician workstation or personal digital assistant and the like. The device 10''' can be configured to measure tension load in a plurality of different positions (e.g., between 0-90 degrees).

Figure 10A:
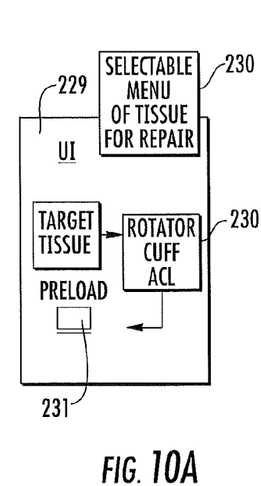
Figures 10B, 10C:
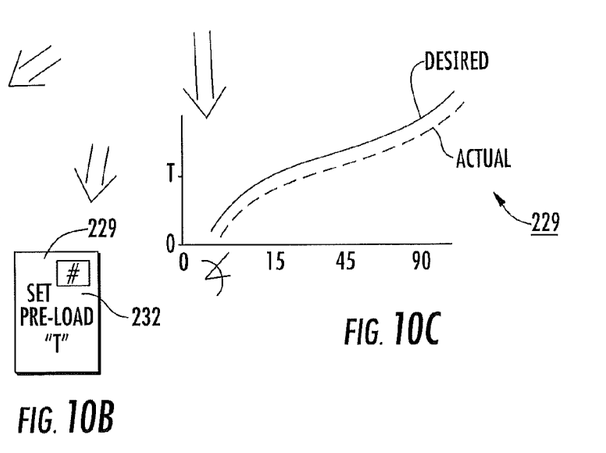

As shown in FIGS. 10A-10B, the device 10''' can be configured to provide a UI (user interface) 229 that allows a user to select the desired tension for a target tissue. The UI 229 can be associated with the remote display 221 and/or the on-board display 21. The UI 229 can be a touch screen, keypad or other entry. That is, the UI 229 can be integrated into the device 10''' or the device 10''' can cooperate with the remote device 228 that includes or communicates with a UI 229. If the latter, the input and/or output can be wirelessly transmitted between the device 10''' and the remote device 228.

FIG. 10A illustrates a UI 229 with a pull-down menu of different target tissues 230 (or the same target tissue but an age or gender input as well). The selection of this parameter 230 can automatically or electronically cause the device 10''' to recognize the target pre-load tension 231 for the patient and select that tension for monitoring as the device reaches this tension "T". An alert (audio and/or visual) can be generated by the device 10''' when the target tension has been reached and/or if the pre-load tension is exceeded.

FIG. 10B illustrates the UI 229 can allow a user to enter a target pre-load tension directly 232 and "set" this value for use during the procedure.

As shown in FIG. 10C, in some embodiments, the on-board and/or remote display 21, 221 can have a UI 229 that displays the measured loads as a graph as shown in FIG. 10C, illustrating Tension versus angle, the angle referring to the angle or orientation of the limb or digit (e.g., finger, thumb, toe). The measured loads can be graphically displayed adjacent target loads.

The device 10''' can include a speaker 225 that can be configured to automatically generate an audible alert such as a tone or a pre-recorded voice/verbal instruction, word(s) or message. The device 10''' may also generate a visual alert (e.g., a flashing light or a "red" light and the like) if a measured tension load exceeds or is under a target tensile load (in one or more orientations) and/or a visual or audible alert if the tension is within the desired range (e.g., a constant light rather than a flashing light, a green light, a different audio or verbal message from that generated when the load is over or under the desired load and the like). The alert can be automatically transmitted or output while the grasper 15 is in the body and engaging tissue. The grasper 15 can be configured to automatically activate the tension measurement device when closed. The grasper 15 can include a proximity sensor or may be configured to define a closed or open circuit when closed to electronically automatically activate the tension measurement device 20. The device can include an on-board power source. The tension measurement device 20 can be in communication with the power source. The power source can be a small battery, such as a pancake type battery or other small battery. The device 10''' may also have an on-board digital camera for generating images of the grasper 15 and/or target tissue during the procedure.

The circuit 120 can include a digital signal processor and/or an Application Specific Integrated Circuit (ASIC) (e.g., ASIC and/or processor with software) that includes or executes part or all of the computer readable program code for generating the tension measurement, readout and/or alert. The circuit 120 or module 220 can include a data processing system which may, for example, be incorporated or integrated into the processor. The processor can communicate with or include electronic memory. The processor can be any commercially available or custom microprocessor. The memory is representative of the overall hierarchy of memory devices containing the software and data used to implement the functionality of the data processing system. The memory can include, but is not limited to, the following types of devices: cache, ROM, PROM, EPROM, EEPROM, flash memory, SRAM, and DRAM.

The processor or memory may include several categories of software and data used in the data processing system: the operating system; the application programs; the input/output (I/O) device drivers; and tension data.

As will be appreciated by those of skill in the art, the operating systems may be any operating system suitable for use with a data processing system, such as OS/2, AIX, or zOS from International Business Machines Corporation, Armonk, N.Y., Windows CE, Windows NT, Windows95, Windows98, Windows2000, WindowsXP, Windows Visa, Windows7, Windows CE or other Windows versions from Microsoft Corporation, Redmond, Wash., Palm OS, Symbian OS, Cisco IOS, VxWorks, Unix or Linux, Mac OS from Apple Computer, LabView, or proprietary operating systems. The I/O device drivers typically include software routines accessed through the operating system by the application programs to communicate with devices such as I/O data port(s), data storage and certain memory components. The application programs are illustrative of the programs that implement the various features of the data processing system and can include at least one application, which supports operations according to embodiments of the present invention. The data represents the static and dynamic data used by the application programs, the operating system, the I/O device driver and the like.

The device 10''' can wirelessly communicate with a workstation and/or other remote computer device 228. The remote device 228 can include a display 221 can communicate with a computer which includes a portal and an Application that allows the tension data to be graphically displayed for a patient record or other data record. The device 10''' can communicate with the remote device 228 via a computer network including an intranet or the internet with the appropriate use of firewalls for patient privacy and compliance with HIPPA (Health Insurance Portability and Accountability Act) or other regulatory rule or authority.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A surgical device, comprising:
  a tissue grasper having a pair of cooperating outer prongs that pivotably close together in parallel relationship in front of a pivot attachment of the prongs, wherein the prongs have outer free ends that are configured to contact tissue to trap target soft tissue therebetween so as to be able to pull soft tissue outwardly and first and second shafts extending away from respective free ends, and wherein the second shaft is a lower elongate shaft and the first shaft is configured to allow a user to push against the first shaft to close the prongs together;
  a tension measurement device in communication with the tissue grasper whereby tension applied to target tissue by the tissue grasper is measured, wherein the tension measurement device comprises an elongate shaft that extends in a longitudinal direction to be longitudinally aligned with and attached to the lower elongate shaft of the tissue grasper;
  an upper platform having opposing first and second end portions, the upper platform configured to support the elongate shaft of the tension measurement device, the upper platform residing below and extending parallel to the elongate shaft of the tension measurement device with the tissue grasper prongs extending above and forward of the first end portion of the upper platform, wherein the tissue grasper is slidably held by the upper platform so as to be able to retract and extend in a lengthwise direction relative to the upper platform, the lengthwise direction being in a direction along a longest dimension of the upper platform;
  a housing slidably mounted to the upper platform with projections extending below the upper platform, wherein the upper platform comprises a slot that extends in the lengthwise direction with the projections extending down through the slot below the upper platform whereby the housing is able to slidably translate back and forth in the slot, and wherein the elongate shaft of the tension measurement device extends through the housing, and the elongate shaft of the tension measurement device is configured to slidably translate relative to the housing in the lengthwise direction; and a limb mounting member attached to and residing under the upper platform, wherein the limb mounting member is an external device that is configured to reside against skin of a patient and is configured to releasably attach to a limb of a patient, wherein the upper platform is pivotably and slidably attached to the limb mounting member to be able to (i) rotate longitudinally and transversely, (ii) slide up and down, and (iii) releasably lock into a desired position relative to the limb mounting member.

2. The surgical device of claim 1, wherein the outer prongs comprise anti-slip surfaces.

3. The surgical device of claim 1, wherein the device is configured to measure a change in length of tissue with or in response to tension applied by the tissue grasper.

4. The surgical device of claim 1, wherein the device further comprises an axially extending threaded member with an external end handle, wherein the threaded member comprises a portion that resides inside the housing and is attached to the tension measurement elongate shaft and extends out of the housing proximate the second end portion of the platform and attaches to the handle, and wherein the threaded member is able to threadably retract and extend in the lengthwise direction relative to the upper platform in response to rotation of the handle.

5. The surgical device of claim 1, further comprising:
a resilient member residing in the housing in communication with the elongate shaft of the tension measurement device; and
a rotatable handle residing outside of the housing in communication with the elongate shaft of the tension measurement device,
wherein the resilient member resides inside the housing and is configured to cooperate with the housing and the elongate shaft of the tension measurement device to apply an adjustable tensile force to the target tissue held by the tissue grasper.

6. The surgical device of claim 5, wherein the resilient member comprises a coil spring that compresses against the housing, and wherein the elongate shaft of the tension measurement device is configured to extend through a channel defined by the coil spring inside the housing.

7. The surgical device of claim 1, wherein the surgical device is configured to allow the limb of the patient to move into or through different positions while the limb mounting member remains in position on a respective patient.

8. The surgical device of claim 1, wherein the upper platform is attached to the limb mounting member using a gimble that resides between the upper platform and limb mounting member to allow the tissue grasper to pivot and lock into position in different orientations.

9. The surgical device of claim 1, further comprising a circuit in communication with the tension measurement device configured to allow a user to select a target pre-load tension and/or provide a defined target pre-load tension to be applied by the device and an on-board display in communication with the circuit configured to show at least one of the following: (a) a user selectable pre-load tension; and (b) a measured tension and/or externally visible indicia of measured tension generated by the tissue grasper.

10. The surgical device of claim 1, wherein the limb mounting member comprises an elongate body with a plurality of straps extending transversely from outer perimeter edge portions thereof.

11. The surgical device of claim 1, further comprising a slidably adjustable mounting arm with a slot that is lockably attached to the limb mounting member to allow for vertical adjustment of the tissue grasper.

12. The surgical device of claim 1, wherein the limb mounting member has a concave contour and is configured to reside against skin of a patient.

13. The surgical device of claim 1, further comprising a circuit in communication with the tension measurement device configured to allow a user to select a target pre-load tension and/or provide a defined target pre-load tension to be applied by the device, wherein the circuit is in communication with the tension measurement device and is configured to generate an alert when a pre-set tension is met and/or exceeded.

14. The surgical device of claim 1, further comprising a circuit in communication with the tension measurement device configured to allow a user to select a target pre-load tension and/or provide a defined target pre-load tension to be applied by the device andwherein the circuit is in communication with a User Interface configured to allow a user to select or enter a desired pre-load tension.

15. The surgical device of claim 1, wherein the tissue grasper and tension measurement device cooperate to: (i) hold a rotator cuff tendon at a target pre-load tension and (ii) hold a tendon at this pre-load tension while a physician attaches the tendon to local bone.

16. The surgical device of claim 15, wherein the limb mounting member is sized and configured as an arm mounting member that is configured to releasably hold the surgical device on an arm of a patient while allowing the tissue grasper to pivot relative to the arm mounting member.

* * * * *

UNITED STATES PATENT AND TRADEMARK OFFICE
CERTIFICATE OF CORRECTION

PATENT NO. : 8,926,626 B2
APPLICATION NO. : 12/942311
DATED : January 6, 2015
INVENTOR(S) : Mannava et al.

Page 1 of 1

It is certified that error appears in the above-identified patent and that said Letters Patent is hereby corrected as shown below:

In the Claims:
Column 12, Claim 14, Line 38: Please correct "andwherein"
to read -- and wherein --

Signed and Sealed this
Thirtieth Day of June, 2015

Michelle K. Lee
*Director of the United States Patent and Trademark Office*